(12) United States Patent
Ansay et al.

(10) Patent No.: US 8,203,330 B2
(45) Date of Patent: Jun. 19, 2012

(54) DISTANCE MEASURING DEVICE

(75) Inventors: Pierre Ansay, Angleur-Liege (BE); Robert Poirrier, Angleur-Liege (BE); Bernard Beckers, Angleur-Liege (BE)

(73) Assignees: Nomics (Societe Anonyme), Angleur-Liege (BE); Logistique Spatiale Wallonne-Wallonia Space Logistics- "W.S.L." (Societe Anonyme), Angleur-Liege (BE)

( * ) Notice: Subject to any disclaimer, the term of this patent is extended or adjusted under 35 U.S.C. 154(b) by 1328 days.

(21) Appl. No.: 10/586,138

(22) PCT Filed: Jan. 17, 2005

(86) PCT No.: PCT/EP2005/050178
§ 371 (c)(1),
(2), (4) Date: May 30, 2007

(87) PCT Pub. No.: WO2005/071353
PCT Pub. Date: Aug. 4, 2005

(65) Prior Publication Data
US 2007/0273366 A1    Nov. 29, 2007

(30) Foreign Application Priority Data
Jan. 16, 2004    (EP) ..................................... 04075045

(51) Int. Cl.
*G01B 7/14*    (2006.01)
*G01B 7/30*    (2006.01)
*G01B 3/30*    (2006.01)
*G01B 21/00*    (2006.01)
*G01R 33/00*    (2006.01)
*G01R 33/02*    (2006.01)
*G01P 21/00*    (2006.01)
*A61B 5/103*    (2006.01)
*A61B 5/117*    (2006.01)

(52) U.S. Cl. ............... 324/207.11; 324/207.13; 73/1.79; 73/1.81; 600/595

(58) Field of Classification Search ................... 600/26, 600/27, 587, 595; 73/1.79, 1.81; 324/207.11, 324/207.13, 207.15, 207.16, 207.17, 207.18, 324/207.19
See application file for complete search history.

(56) References Cited

U.S. PATENT DOCUMENTS
3,200,399 A * 8/1965 Tschannen et al. ........... 342/125
(Continued)

FOREIGN PATENT DOCUMENTS
DE    41 14 398 A    10/1992
DE    4114398 A1 *    10/1992
FR    2 692 979 A    12/1993

OTHER PUBLICATIONS
Machine Translation of DE 41 14 398 A1.*

*Primary Examiner* — Max Hindenburg
*Assistant Examiner* — Adam Eiseman
(74) *Attorney, Agent, or Firm* — Jacobson Holman PLLC

(57) ABSTRACT

Distance measuring device comprising an emitter and a receiver, said emitter being arranged to produce a magnetic field by means of a resonant circuit having a resonant frequency, said receiver being arranged to pick up at said resonant frequency the magnetic field emitted by the emitter and convert the strength of the magnetic field picked up into a first signal having an energy value, said emitter being arranged to produce said magnetic field intermittently, each emission having a predetermined energy, said receiver being connected to a detector arranged to determine, by correlation of said first signal with a second predetermined signal having a waveform representative of a signal to be picked up by the receiver, a distance measurement signal representing the distance between the emitter and the receiver. The device finds its application in detectors for sleep disorders or other forms of illness.

19 Claims, 15 Drawing Sheets

U.S. PATENT DOCUMENTS

| | | | | |
|---|---|---|---|---|
| 4,665,361 | A | * | 5/1987 | Dorsch et al. ............ 324/207.15 |
| 4,843,259 | A | * | 6/1989 | Weisshaupt .................... 327/510 |
| 6,032,065 | A | * | 2/2000 | Brown .......................... 600/383 |
| 6,234,654 | B1 | | 5/2001 | Okuchi et al. |
| 6,656,135 | B2 | * | 12/2003 | Zogbi et al. .................... 600/594 |
| 6,879,921 | B2 | * | 4/2005 | Bogel et al. ...................... 702/97 |
| 2002/0115944 | A1 | | 8/2002 | Mendes et al. |
| 2005/0104577 | A1 | * | 5/2005 | Matei et al. .............. 324/207.13 |

* cited by examiner

Time (arbitrary units)

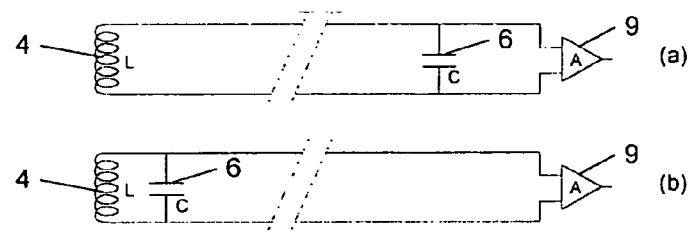
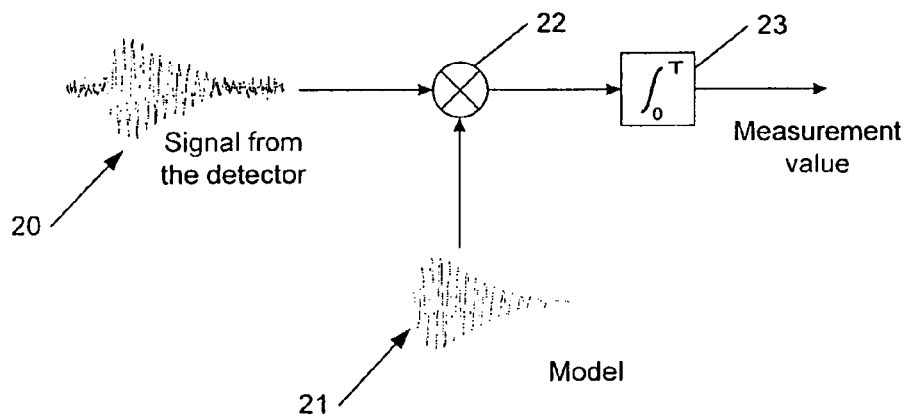
Fig. 5
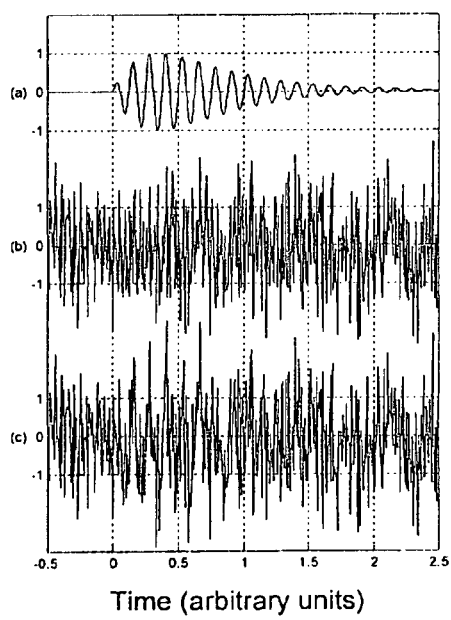
Time (arbitrary units)
Fig. 6
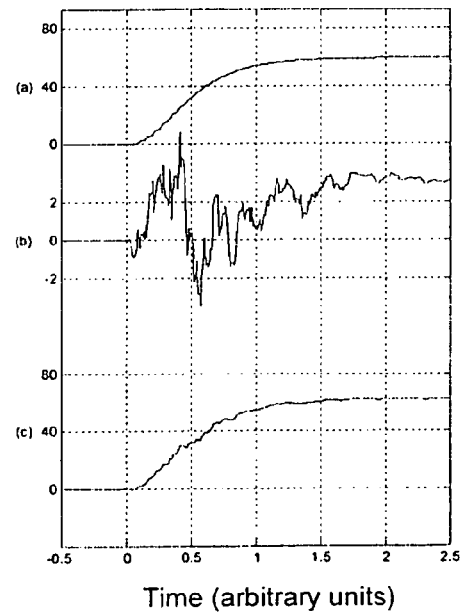
Time (arbitrary units)
Fig. 7

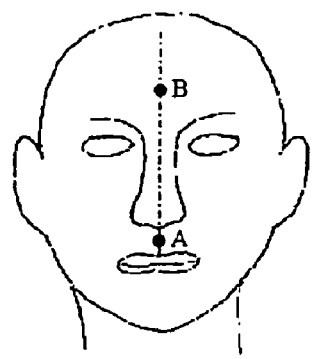
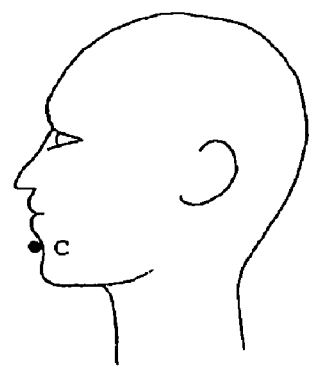
Fig. 12
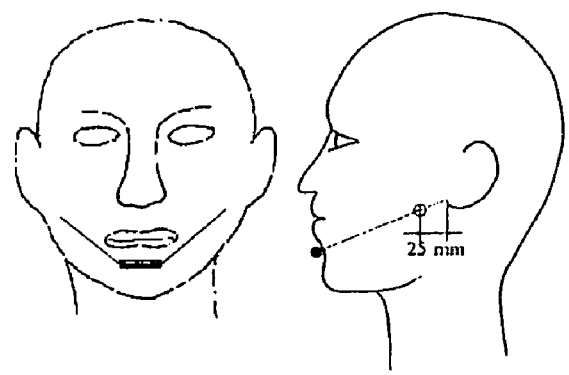
Fig. 13

|  | SCEvent | FCEvent | NEBEvent | LMOEvent |
|---|---|---|---|---|
| Hypopnea | 0 | 1 | 0 | 0 |
| Obstructive apnea | 1 | 0 | 0 | 0 |
| Mixed apnea | 1 | 0 | 1 | 0 |
| Central apnea | 0 | 0 | 1 | 0 |
| UARS | 1 | 0 | 0 | 1 |

*Fig. 20*

DISTANCE MEASURING DEVICE

The invention concerns a distance measuring device comprising an emitter and a receiver, said emitter being arranged to produce a magnetic field by means of a resonant circuit having a resonant frequency, said receiver being arranged to pick up at said resonant frequency the magnetic field emitted by the emitter and convert the strength of the magnetic field picked up into a first signal having an energy value, said emitter being arranged to produce said magnetic field intermittently, each emission having a predetermined energy, said receiver being connected to a detector arranged to determine a distance measurement signal representing the distance between the emitter and the receiver.

The invention also concerns a sleep disorder detector comprising a distance measuring device.

Such a device is known from the patent application DE 41 14 398. According to the known device, the strength of the magnetic field picked up gives a measurement of the distance between the emitter and the receiver and can in this way be used to measure a distance between two points. To obtain this distance the first signal is amplified selectively.

One drawback of the known device is that it is not adapted to reliably and accurately measure distances of more than a few centimeters without having to use a high-strength magnetic field. Moreover the selective amplification of the first signal not being stated precisely, it does not allow an accurate determination of the distance, in particular when the first signal comprises an amount of noise and interference. For this reason this known device is not able to reliably measure movements of the mouth of a living being in applications where high resolution is required. This is because high-power magnetic fields are not suitable to be used frequently on living beings without having a detrimental effect on the health of that living being.

The aim of the invention is to produce a distance measuring device that is capable of measuring distances very accurately, in particular on the human body, without having to use a value of magnetic field that would be too strong for the human body.

To this end a device according to the invention is characterized in that said detector is arranged to determine said distance measurement signal by correlation of said first signal with a second predetermined signal having a waveform representative of a signal to be picked up by the receiver, said second signal comprising a time window having a predetermined duration and comprising at least an initial sub-period, an intermediate sub-period and a final sub-period, said second signal being an alternating signal synchronized with the first signal and whereof the amplitude is attenuated during the initial and final periods and substantially at a maximum during the intermediate period. The use of an alternating signal whereof the amplitude is attenuated during the initial and final sub-periods makes it possible to considerably reduce the noise and interference appearing in frequency ranges far from the resonant frequency. The fact that the amplitude is substantially at a maximum during the intermediate period, that is to say where the first signal reaches its maximum value, makes it possible to considerably reduce the noise and interference in the frequency ranges very close to the resonant frequency whilst making maximum use of the amplitude of this signal during this intermediate sub-period and therefore to be able to work with magnetic fields whereof the power remains low and therefore without damage to the human body.

A first preferential embodiment of a device according to the invention is characterized in that said detector is arranged to implement said correlation by multiplication and integration with said second signal, which second signal is formed by said waveform representing a sinusoidal waveform in synchronization with the first signal itself multiplied by a Tukey window with reduced taper factor. This allows rejection of noise and interference outside the detection frequency.

A second preferential embodiment of a device according to the invention is characterized in that said emitter is housed in a case and arranged to produce said magnetic field outside said case with a power less than 1 mTesla, preferably less than 1 µTesla. This embodiment is particularly adapted to the human body.

A sleep disorder detector according to the invention is characterized in that said device is mounted on a support arranged to be applied onto the head of a living being so as to measure movements of the mouth.

The invention will now be described in more detail with the help of the drawings that depict a preferential embodiment of a device according to the invention and a sleep disorder detector comprising a distance measuring device according to the invention. In the drawings:

BRIEF DESCRIPTION OF THE DRAWINGS

FIG. 4 illustrates two examples of the receiver circuit;

FIG. 5 illustrates the principle of detection by correlation of the signal with a model of the signal to be detected;

FIGS. 6 and 7 show an example of a received signal and of the signal obtained after detection by correlation;

FIGS. 12 and 13 show the placing of the device on a living being;

FIG. 20 shows a table used to determine apneas;

Figure 1:
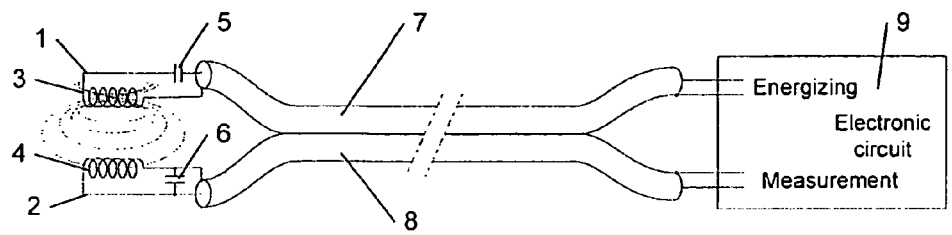
FIG. 1 illustrates the basic structure of the measuring device.

In the drawings, the same reference has been assigned to the same element or a similar element.

The distance measuring device uses a robust distance sensor for physiological use. Its magnetic principle offers many measurement possibilities, since it is not affected by the presence of clothing or resting against a pillow or a mattress (in applications during sleep), nor by the state of restlessness or perspiration of the living being onto whom it is applied. The magnetic field necessary for the measurement is extremely small. The field emission is periodic, at the measuring rate, with an extremely small cyclic ratio, while its maximum amplitude reaches a value less than 1 mTesla, preferably less than 1 µTesla, perhaps even of the order of 0.4 µTesla, considered to be non-harmful to health in the event of continuous exposure.

The sensor is designed to operate with loose magnetic coupling, which means that the emitter affects the receiver, but the attenuation between the emitter and the receiver does not allow the receiver to affect the emitter in return. The detection method is efficient and based on detection by correlation which makes it possible, despite the very low level of the emitted magnetic field, to extend the measurement range in a distance ratio going up to 5, perhaps even 6, times greater than the known devices. Higher distance ratios can be achieved by increasing the emitted field in order to limit the effect of interference. According to application, the sensor can be implemented with components of very small size for distances ranging from 5 to 30 mm, or induction coils of medium size (less than 10 mm in diameter and less than 15 mm long) for a measuring range of 7 to 35 cm while keeping a magnetic field with maximum amplitude less than 1 µTesla. The characteristics of this sensor make it possible to easily implement an ergonomic system with easy placing by the subject themselves, so that it can be used in ambulatory applications.

Several distance measurements with respect to the same reference are possible using a single magnetic emission circuit. Bilateral energizing of the magnetic emission circuit also makes it possible to use this device for transmission of information at low transmission speed and short distance. Simultaneous measurement of the communication distance in particular finds safety applications. Obtaining still higher performances, in both measurement and transmission reliability, is possible by giving the emitted magnetic field a pseudorandom nature.

FIG. 1 illustrates an example of a basic structure of a device according to the invention. The device comprises an emitter 1 and a receiver 2 intended to be placed at a distance from one another. The emitter comprises an induction coil 3 connected in series with a capacitor 5, whilst in the receiver the induction coil 4 and the capacitor 6 are connected in parallel. The emitter 1, respectively the receiver 2, are connected by means of a cable 7, respectively 8, to a conditioning and measuring unit 9. The unit 9 comprises a detector and an energizing circuit as will be described below. The sensors used use the property that a resonant circuit has of energizing another one tuned to the same frequency, through their mutual induction coil (3, 4). The use of resonant circuits rather than simple induction coils significantly improves both the performance of the energizing circuit and the sensitivity of the sensor. The use of simultaneous connection of the emitter and the receiver to the same electronic circuit makes it possible to simplify the device by avoiding synchronization errors. In this case, for matters of comfort, the cables are generally gathered together over the major part of their length, to separate only at the approach to the measuring elements. However, the emitting and receiving circuits can be disassociated without undermining the measuring principle.

Figure 2:
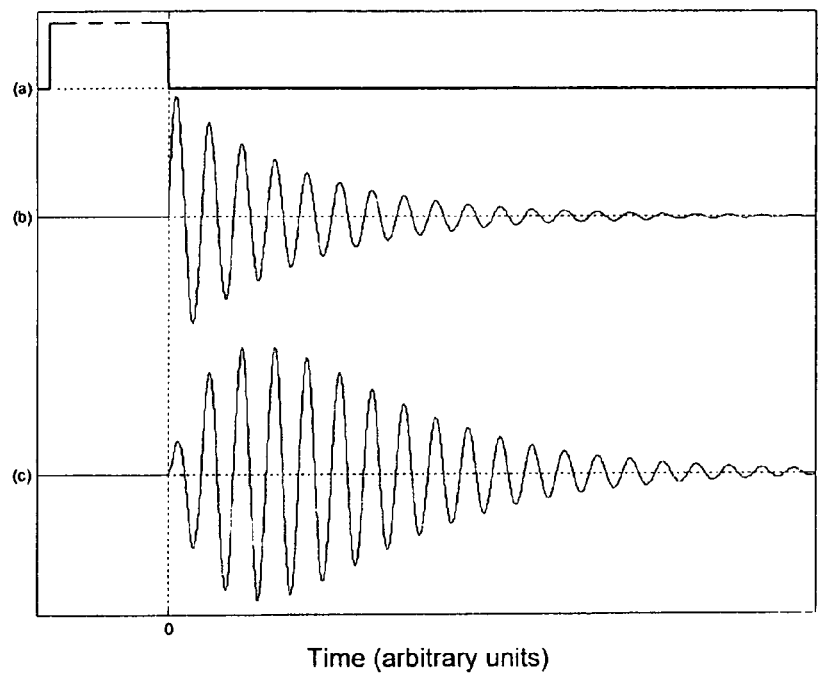
FIG. 2 illustrates the energizing of the emitter and the signal emitted by the emitter and the signal received by the receiver.

In order to limit the mean magnetic field emitted, and thus avoid induction in the long term of effects that are harmful or even simply a nuisance to the patient, and in order to reduce electrical consumption, the resonant emission circuit is energized selectively each time a measurement is taken, as illustrated in FIG. 2. A current pulse, as illustrated at 2a, is produced by the energizing circuit in order to energize the emitter by means of an electrical current. The current flowing in the emitting induction coil 3, and which is proportional to the emitted magnetic field, takes a form that is slightly different depending on the energizing mode adopted, but of general appearance as depicted in FIG. 2b. The voltage obtained at the receiver 2, in the event of compatibility of the resonant circuits, appears as in FIG. 2c. Resonance occurs following closure of the resonant circuit at time 0, after a prior initialization period shown at (a), the purpose of which is to create a voltage at the terminals of the capacitor and/or a current in the induction coil.

The envelope of this signal depends on the quality factor of the resonant circuits used. In the event of poor compatibility of the resonant circuits, this envelope can be significantly modified, with the possible appearance of a beat phenomenon. The maximum value of the voltage observed at the receiver varies as a function of the distance between emission induction coil 3 and receiving induction coil 4 according to the relationship:

$$V=(\alpha/d^3)+\beta \quad (1)$$

where $\alpha$ is the overall detection gain, including the effect of the amplifiers, $\beta$ a possible offset due to the detection circuits and d the distance between the emitter and the receiver.

In the preferred embodiment of the invention, the resonant circuits are tuned to a frequency of 5 to 8 kHz, so as to maximize the quality factor of the resonant circuits whilst remaining below the radio frequencies. The use of miniature induction coils can however lead to the adoption of frequencies going up to 50, perhaps even 100, kHz, according to the capabilities of the detection circuit. The value and size of the resonance induction coils are adapted so as to be able to base the detection on a signal having 10 to 30 periods of resonance of significant amplitude. Shorter durations degrade the detection performance, whilst larger values require too great an accuracy, in practice, in the tuning of the resonant circuits.

Figure 3:
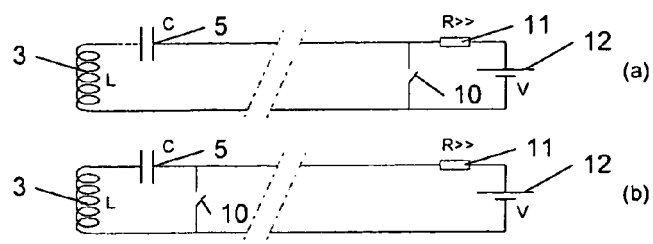
FIG. 3 illustrates various energizing topologies for a series resonant circuit forming the emitter.

Various topologies can be adopted for the energizing circuit. The choice must take into account the desired energizing level (maximum amplitude of the magnetic field), the stray coupling existing between the wires 7 and 8 leading from the unit 9 to the emitter and receiver (especially during the use of very thin cables for the comfort of people), and electromagnetic compatibility aspects. Various topologies of a series resonant circuit are presented in FIG. 3. The energizing circuit comprises a resistor 11, a switching element or switch 10 and a voltage source 12 connected in series through electrical conductors 7 in series with the induction coil and the capacitor. Energizing is performed by a brief closure of the switch 10 during which the capacitor 5 is charged to the supply voltage and a current is created in the induction coil 3. At the moment the switch 10 is opened, the circuit formed by the induction coil 3 and the capacitor 5 therefore starts to oscillate under the effect of these two initial conditions. The main attraction of this method is that it is easy to obtain high or even variable energizing levels, according to the time of closing the switch. The circuits illustrated in FIG. 3 are so-called "regeneration" serial energizing circuits. Energizing is achieved by closure of the switch 10, which remains closed throughout the measurement. The opening of the switch then allows the capacitor 5 to recharge without oscillation through the resistor 11. The embodiment illustrated in FIG. 3a facilitates the control of the switch, while the embodiment 3b makes it possible to both make the voltage in the cable zero and make the current in the cable constant during the measurement. These embodiments make it possible to avoid stray coupling in the cables, since the closed switch imposes a very small voltage in the cable of the emitter during the measurement.

Moreover the embodiment of FIG. 3a offers the advantage that the switch is easier to control since it is situated close to the source 12 present in the unit 9.

Series resonance energizing can be achieved in two main forms, namely alternating energizing and single energizing with regeneration. Alternating energizing consists of driving the resonant circuit by means of a source of voltage of square appearance. Energizing is achieved at each transition of the voltage source, but the sign of the electromagnetic field emitted during a falling transition is the inverse of that observed during a rising transition. It is imperative that this effect be compensated for at the detection circuit in order to avoid measurement inaccuracies. Single energizing with regeneration consists of slowly charging the capacitor of the resonant circuit through a high-value resistor in order to avoid resonance, then closing the switch during the entire measurement in order to allow the resonant circuit thus formed to oscillate freely.

The preferred embodiment of the invention therefore uses energizing with regeneration with a capacitor integrated into the emission element (FIGS. 3a and b). This makes it possible to maintain a theoretically zero voltage all along the cable during the measurement. The topology with decentralized energizing (FIG. 3b) has in addition the advantage of a constant current during the measurement.

The emitter is arranged to produce a magnetic field by means of the resonant circuit formed by the induction coil 3 and the capacitor 5. The resonant circuit has a resonant frequency and the receiver is arranged to pick up at said resonant frequency the magnetic field emitted by the emitter and convert the strength of the magnetic field picked up into a first signal having an energy value. As illustrated in FIG. 2a, the emitter produces the magnetic field from a pulse supplied at the energizing circuit. Thus this magnetic field is produced intermittently and each emission has a predetermined energy, in particular determined by the value of the induction coil and of the capacitor.

FIG. 4 illustrates two examples of the circuit of the receiver 2, in particular (4a) with integrated capacitor and (4b) with remote capacitor. The receiver is arranged to pick up at the resonant frequency the magnetic field emitted by the emitter and convert the strength of the magnetic field picked up into a first signal having an energy value that represents the energy picked up by the receiver. Choice of detection method, that is to say use of the observed voltage to obtain an image of the distance, is essential to minimize the required field values, and thus the possible harmful effects on people. Detection is performed by correlation as will be described below.

If a minimum measuring distance is complied with where the coupling between the emission 3 and receiving 4 induction coils is sufficiently loose, it can be considered that the waveform of the received signal is modified only in amplitude as a function of the distance. This entire waveform can therefore be used to improve the detection. One known method proceeds by implementing a synchronous detection. This method consists of multiplying the received signal by 1 when the theoretical waveform is considered positive, and by −1 when it is considered negative, and then integrating the signal thus obtained. Another known method proceeds by implementing a "lock-in" type detection, which consists of multiplying the received signal by a sinusoid synchronized with the received signal, so that the positive alternations of the sinusoid correspond to the positive alternations of the signal to be received, and the negative alternations of the sinusoid correspond to the negative alternations of the signal to be received, and then of integrating the signal thus obtained. These synchronous or "lock-in" detection methods are depicted in analog form, but can just as easily be performed digitally. This synchronous detection is a form of implementation of detection by correlation of the signal picked up by the receiver with a second predetermined signal having a waveform representative of a signal to be picked up by the receiver. The result coming from this correlation then constitutes a distance measurement signal representing the distance between the emitter and the receiver. Detection by correlation consists of multiplying the received signal by a model, possibly modified, of the theoretical waveform, and then integrating the signal thus obtained. The value obtained at the end of the integration time is the measurement sought. This generic method has the advantage of integrating as a particular case the known methods of synchronous detection, "lock-in" and adapted filtering, according to the form given in the detection model. The general principle is depicted in FIG. 5, and its effectiveness for the detection of a noisy signal is illustrated in FIG. 6. The signal picked up 20 is multiplied (22) by a second signal 21 and the result of this multiplication is integrated (23) in order to provide the measurement value. FIG. 6a shows an example of a second signal (21), FIG. 6b an example of the noise alone, at a relative level, with respect to the signal picked up, corresponding to typical detection conditions at two thirds of the received signal measurement range and FIG. 6c depicts the real situation where the signal picked up is combined with the noise. FIG. 7 depicts the result of the integration during detection by correlation. References a to c in FIG. 7 correspond to those of FIG. 6. It can therefore be noted in FIG. 7c that the measurement signal increases to reach a level corresponding to the distance between emitter and receiver.

Figure 22:
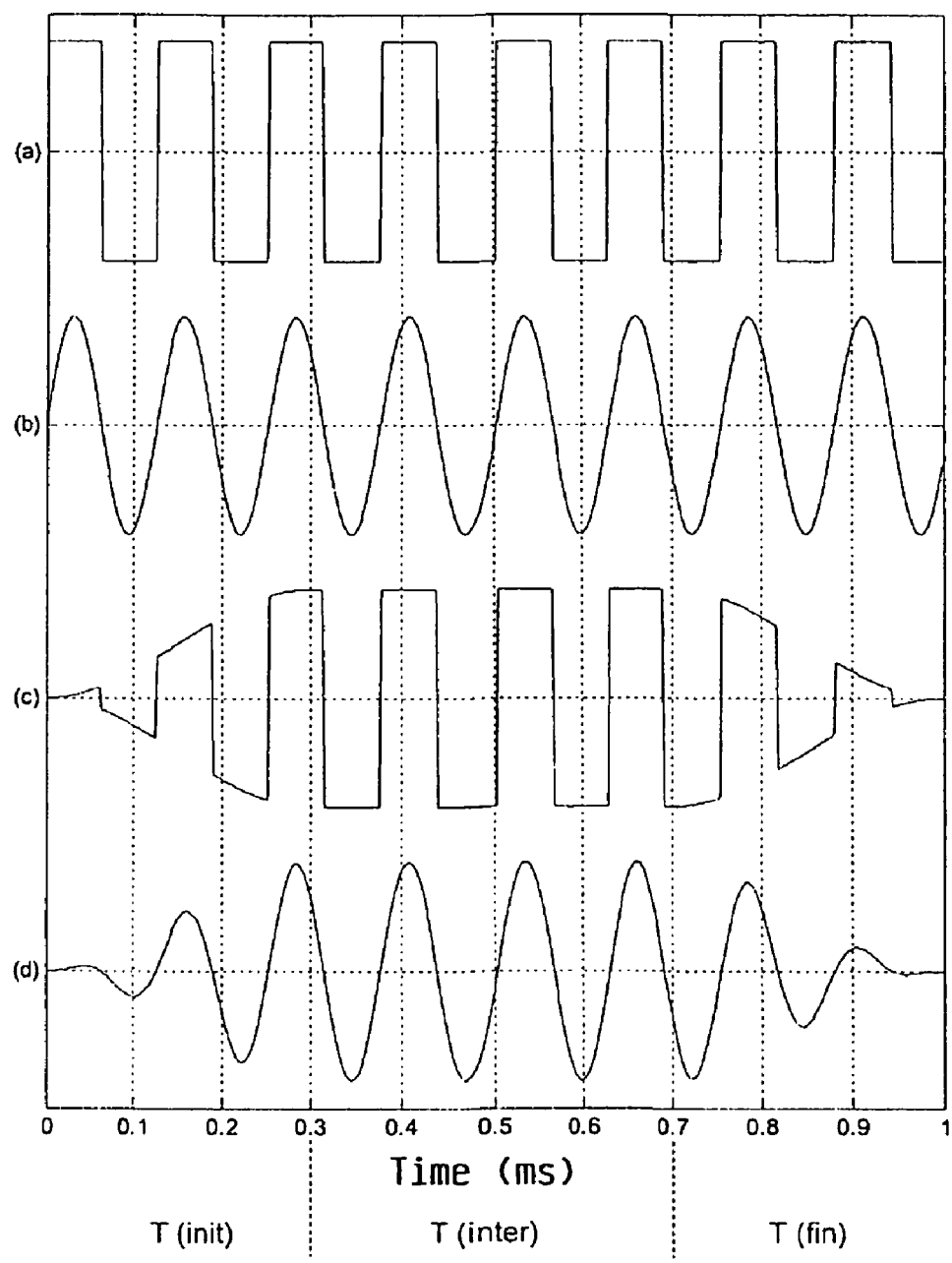
FIGS. 22 a and b show the models corresponding to the conventional synchronous and "lock-in" detection techniques, while FIGS. 22 c and d show two examples of models as used in the present invention.

The known synchronous or "lock-in" detection methods can be implemented in the form of detection by correlation using as the second signal the models presented in FIG. 22 a and b, respectively. The present invention consists of using, as the second signal, an alternating signal synchronized with the first signal coming from the signal picked up by the receiver. This alternating signal comprises a time window having a predetermined duration (T) as illustrated in FIGS. 22 c and d. The time window comprises at least an initial sub-period T(init), an intermediate sub-period T(inter) and a final sub-period T(fin). The model has an amplitude that is attenuated in the sub-periods T(init) and T(fin), and an amplitude substantially at a maximum during the intermediate sub-period T(inter). The model of FIG. 22c corresponds to an adaptation according to the present invention of the synchronous detection method. The model of FIG. 22d corresponds to an adaptation according to the present invention of the "lock-in" detection method.

Figure 23:
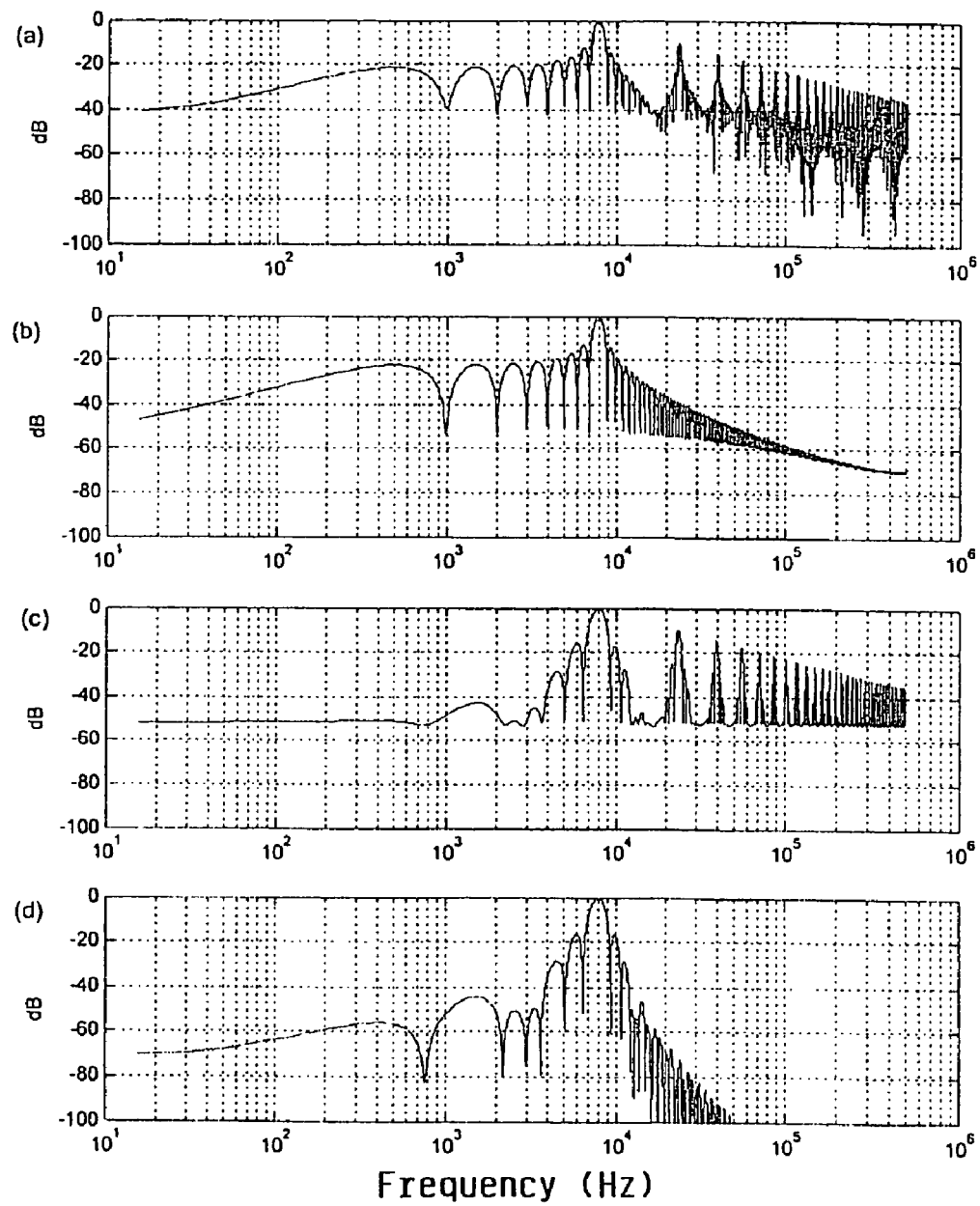
FIG. 23 shows the frequency response of the models reproduced in FIGS. 22 a to d.

FIG. 23 illustrates the advantage of the invention over the known methods through the frequency detection characteristics, FIGS. 23 a to d corresponding to the models of FIGS. 22 a to d, respectively. FIGS. 23 c and d show clearly that the attenuation of the noise and interference present outside the useful band of the signal, here set at 8 kHz, is greater than that obtained with the known methods.

Figure 8:
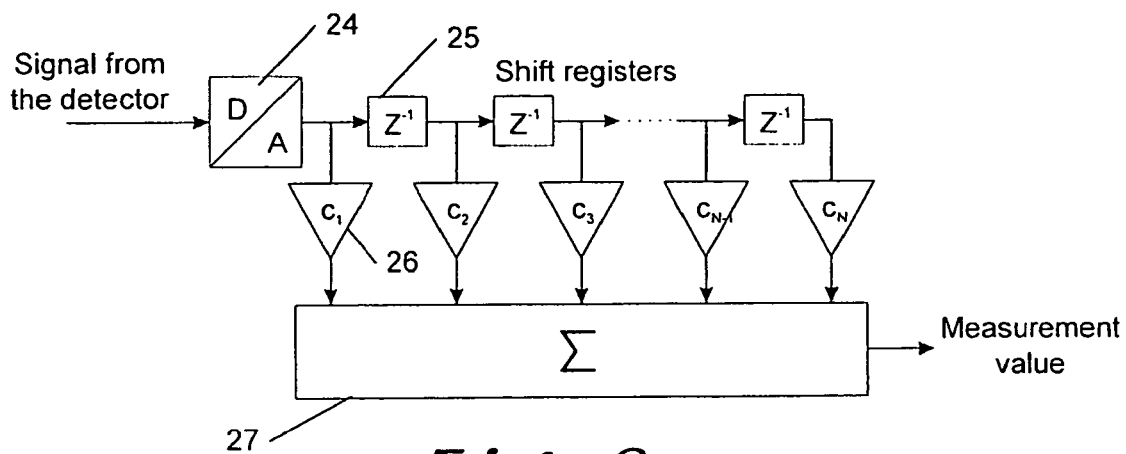
FIG. 8 shows a digital implementation of detection by correlation.

Adapted filtering, which is a form of implementation of detection by correlation, is a technique used in telecommunications, and is considered to provide the best signal to noise ratio assuming white Gaussian noise. Experimentation has shown that this method is also excellent within the context of this invention. It is furthermore accurate if the use of adaptive filters which pose measurement calibration problems is precluded. The adapted filter technique consists of applying to the received signal a filter whereof the pulse response is the inverted image of the theoretical waveform of the signal to be received, and then sampling the signal obtained at a precise moment corresponding to the perfect alignment of the useful signal and the filter. In other words, it can also be said that the result of the measurement is the value of correlation between the portion of the signal where the useful signal is known to be situated, and the theoretical waveform of this useful signal. Given the complexity of the waveform to be produced, this filtering is carried out digitally. The digital application of this principle is depicted in FIG. 8. The received signal is converted (24) into digital after sampling and its values stored in N samples in shift registers 25. These samples are then multiplied (26) by the coefficients $c_i$ representing the detection model, and the results are added together to provide the measurement signal. Integration in the present description therefore means both its mathematical meaning and its digital implementation.

Figure 9:
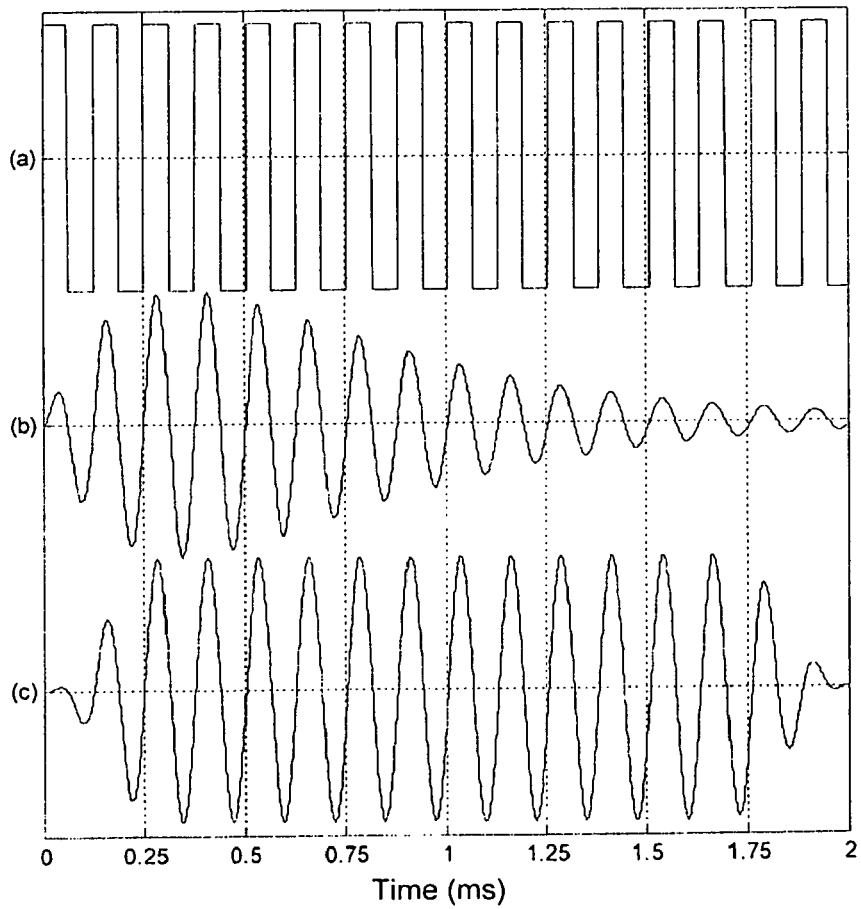
FIG. 9 shows a model corresponding to a generally known detection method and two preferential models, usable for detection by correlation.

FIG. 9 shows models usable for detection by correlation. As a reference, the model (FIG. 9a) of the second signal for synchronous detection is shown. The model for an adapted filtering detection (FIG. 9b) is the theoretical waveform itself, which represents the signal to be picked up as obtained in the absence of perturbations. This waveform possesses the characteristics satisfying the present invention. The model (FIG. 9c) used in a preferred embodiment of the invention is a sinusoidal wave in synchronization with the theoretical waveform, multiplied by a Tukey window with reduced taper factor (typically of the order of 0.2 to 0.4) in order to smooth the transitions. The principle of the Tukey window is described in Harris, F. J. "On the use of windows for harmonic analysis with the discrete Fourier transform" and published in Proceedings of the IEEE, Vol. 66, January 1978, pages 66 to 67.

Figure 10:
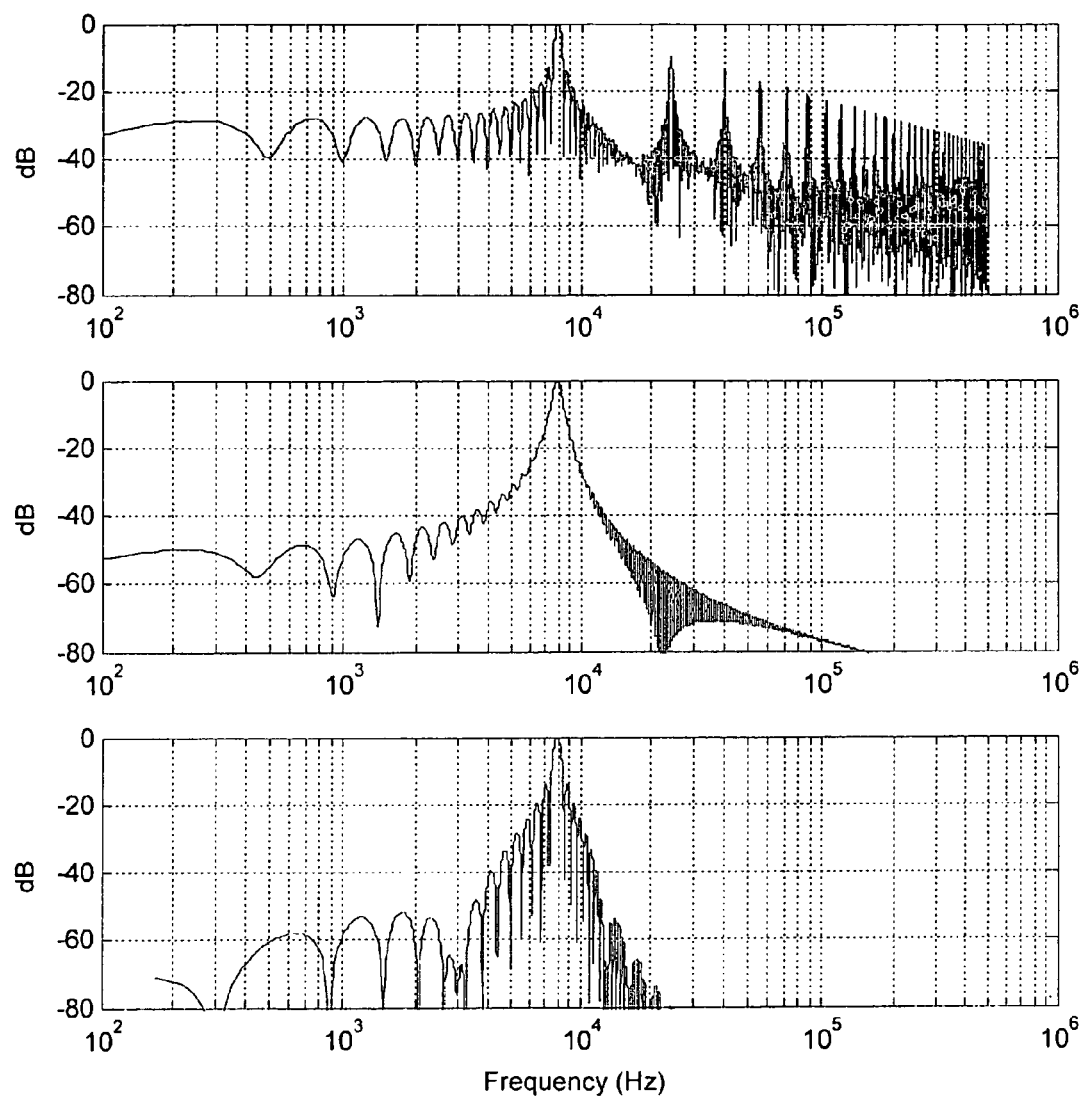
FIGS. 10 and 11 show the noise and interference rejection properties of these three methods of detection by correlation.
Figure 11:
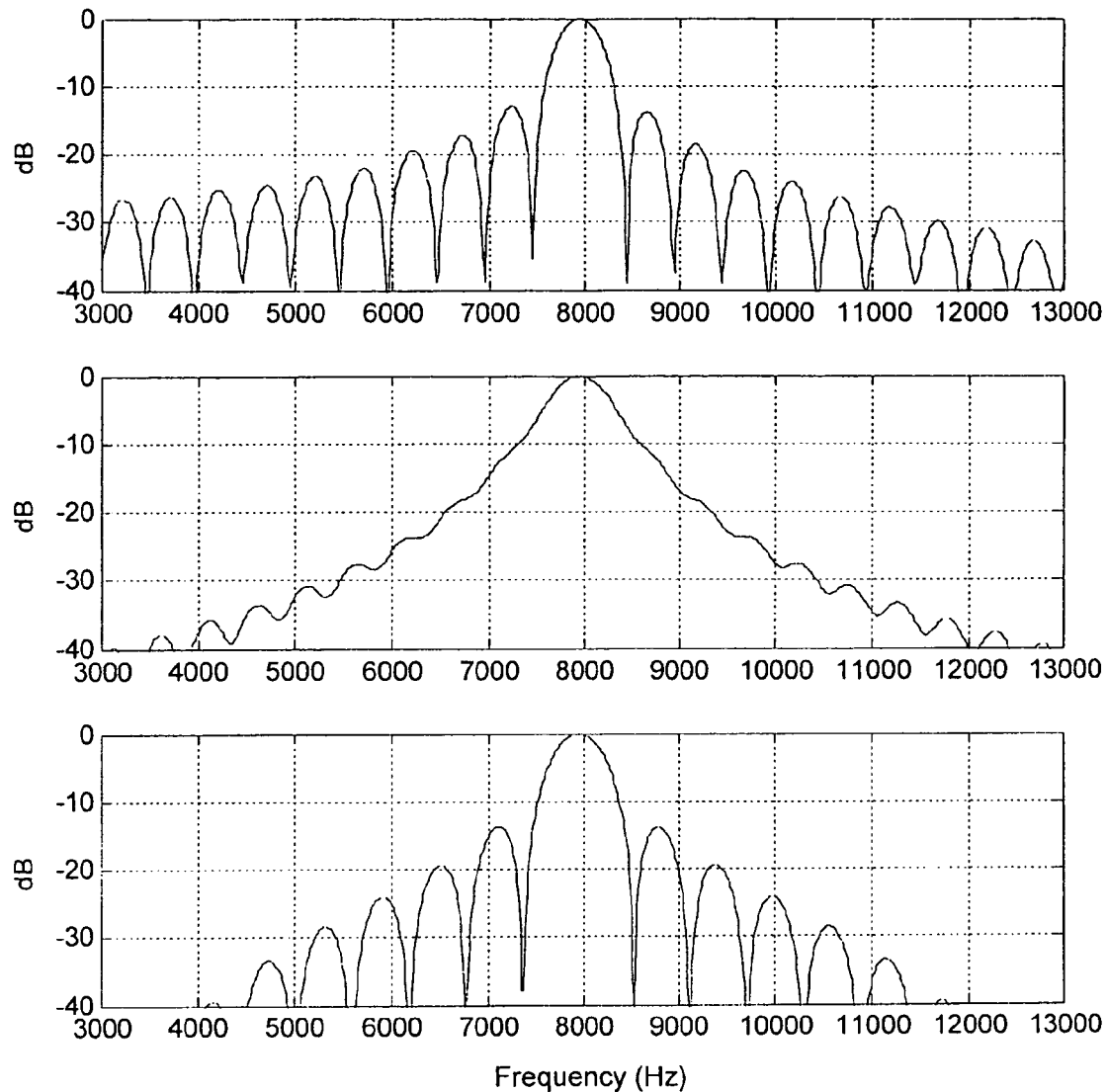

The advantage of this model lies in the properties of rejection of noise and interference outside the detection frequency. The spectral characteristics of these three methods are depicted in FIGS. 10 and 11, respectively. FIG. 10 shows the overall detection spectrum of the different detection models of FIG. 9: synchronous detection (at the top) as a reference, adapted filter (in the middle) and sinusoidal filter with adapted frequency (at the bottom). FIG. 11 shows the detection spectrum around the resonant frequency of the different detection models of FIG. 9: synchronous detection (at the top) as a reference, adapted filter (in the middle) and sinusoidal filter with adapted frequency (at the bottom). The adapted filter shows itself more effective than synchronous detection outside the passband, thus satisfying the characteristics of the present invention, but less effective for frequencies close to that of resonance. The synchronous sinusoidal model shows itself overall the most effective, thus proving its advantage and the usefulness of the present invention.

Obtaining the appropriate model for detection with a particular sensor is achieved during a calibration procedure consisting of placing the two elements of the sensor at a reasonably small distance, so as to obtain a good quality signal. The reception quality is also improved by taking the mean of this signal over several measurements. The waveform obtained can thus be used to derive, in a trivial manner, each of the waveform models presented.

Performances obtained with a sensor optimized for operation between 2.5 and 10 cm:

| | Reference distance | | | |
|---|---|---|---|---|
| | 30 mm | 50 mm | 80 mm | 100 mm |
| Accuracy | 0.3% | 0.5% | 0.2% | 0.1% |
| Standard deviation due to noise | 0.003 mm | 0.05 mm | 0.30 mm | 0.73 mm |

Performances obtained with a sensor optimized for operation between 7.5 and 22 cm:

| | Reference distance | | | | |
|---|---|---|---|---|---|
| | 75 mm | 115 mm | 155 mm | 195 mm | 230 mm |
| Accuracy | 0.3% | 0.7% | 0.1% | 0.5% | 1.8% |
| Standard deviation due to noise | 0.039 mm | 0.12 mm | 0.28 mm | 0.56 mm | 0.91 mm |

Storage of the adapted filter waveforms in a memory placed in the connector of the sensor is used to make calibration of the sensor and of the measurement circuit independent, and thus arrange that any sensor whatsoever (at the time of a replacement, for example) can be connected to the circuit while obtaining the same results. Another storage method is in the memory of the microcontroller placed on the measurement circuit. But in this case it is necessary to re-calibrate each time a sensor is changed.

Various applications of the measuring device according to the invention will be described below. It must be noted however that the use of the measuring device according to the invention is preferential, but that these applications can also be implemented with other measuring devices. One application of the measuring device according to the invention is that to a sleep disorder detector. The device is then mounted on a support arranged to be applied onto the head of a living being so as to measure movements of the mouth. The operating parameters of the sensor are adjusted to produce a peak-to-peak measurement noise less than 1 mm for mouth openings up to 5 cm compared with the mouth closed position. The measurement reference can be placed anywhere along the median line of the face, above the upper lip, as shown in FIG. 12. A common implementation of the invention places this reference under the nose (A). Another common implementation places this reference on the forehead (B). Alternatively, the reference point can be placed inside the mouth, on the teeth, palate or gums. The measurement point of the sensor must be placed so as to monitor the movements of the mandible as well as possible. In the preferred implementation of the invention, it is placed in the hollow under the lower lip (FIG. 13), where the relative movements between the bone structure and the skin are smallest. Alternatively, the measurement point can be situated at the point of the chin, under the chin, or inside the mouth, on the teeth or gums. In the preferred embodiment of the invention, the two elements of the sensor are held in place by means of a comfortable harness, small in size and easily positioned. Supporting the reference point can be performed by any known means. Supporting the measuring point is more difficult. To minimize discomfort for the patient, structures situated close to the mouth and on the cheeks must be very light. Moreover, effective support over the whole opening dynamics should be ensured without imposing any force on the mandible which would risk affecting the measurements. Finally, independence as regards movements of rotation and inclination of the head forwards or backwards is essential. The preferred embodiment of the invention has a sensor structure of elongated shape provided with a link imposing a small traction from the hollow situated under the lower lip along a line passing under the ear lobe, with a fixing point situated at least 25 mm in front of the lobe. Alternatively, an additional support for the sensor can be provided by a chin strap.

Another positioning possibility consists of placing a sensor on the eyelids and another close to the eye, the aim being to measure the movements of the eyelids (a technique also used for detecting drowsiness). In order to study Periodic Limb Movement (PLM) the sensor is placed either side of a joint, the aim being to measure the variations in distance of this joint. Another application would be to say that the sensor can be used for the transmission of data at short distance.

The detection of sleep respiratory disorders is one of the applications of the device according to the invention. The monitoring of respiratory disorders during sleep also applies in the case of patients under positive air pressure treatment. Here, the analysis carried out of the opening of the mouth signal is used for real time adjustment of the value of the pressure supplied by the PAP apparatus.

Figure 14A:
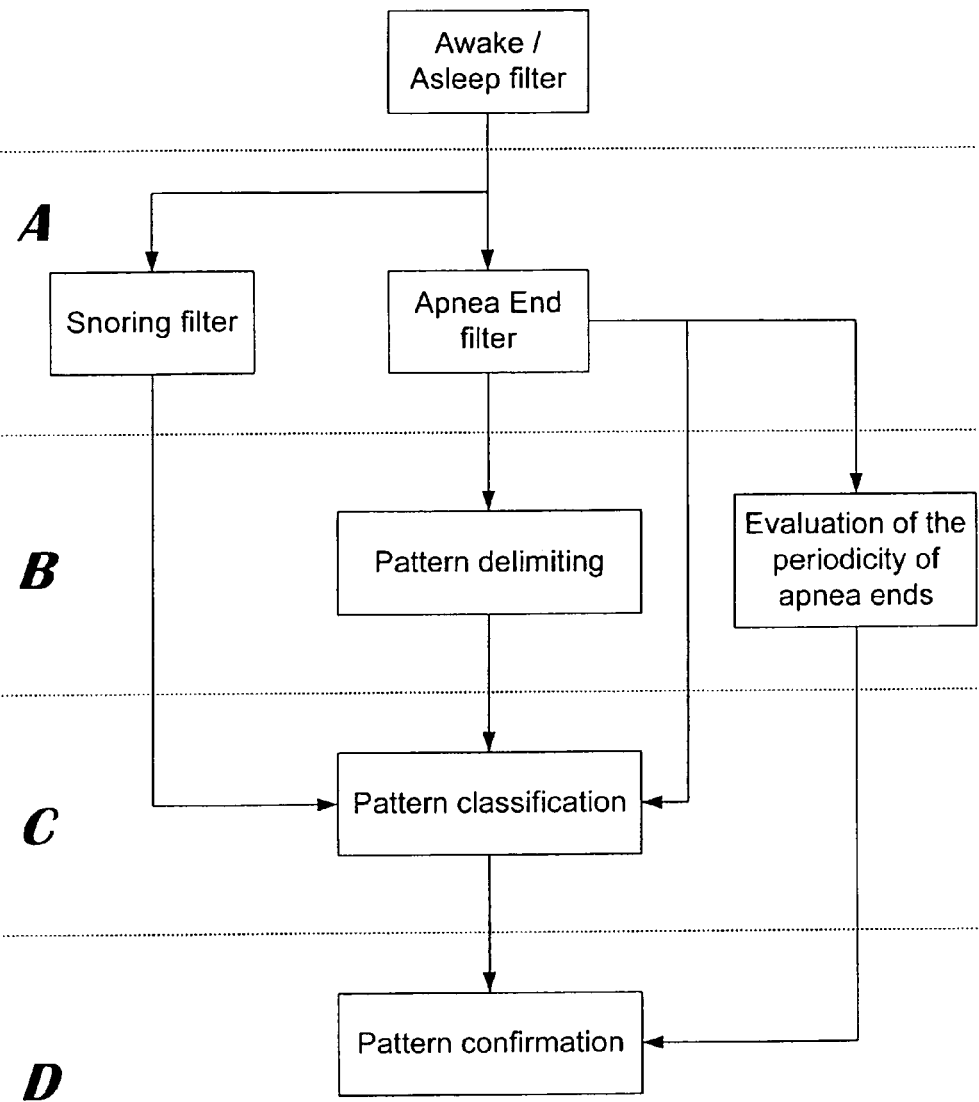
FIGS. 14a), 14b) and 15 illustrate by means of a flow diagram a way of detecting sleep disorders.

In this application, signal processing techniques are used so as to detect all sleep respiratory disorders. The starting point is the data from the sensors and additional signals are derived by filtering. It is the combination of these signals that reveals the various sleep respiratory disorders: central (or Cheynes-Stokes) apnea, mixed apnea, obstructive apnea, hypopnea and upper airways resistance syndrome (UARS). The schematic diagram is described of these sleep respiratory disorders are illustrated in FIGS. 14a), 14b) and 15. The aim of the analysis is therefore to determine whether the pressure applied is sufficient, correct or excessive. This information is used to determine the necessary pressure adjustments and send them to the CPAP.

Figure 15:
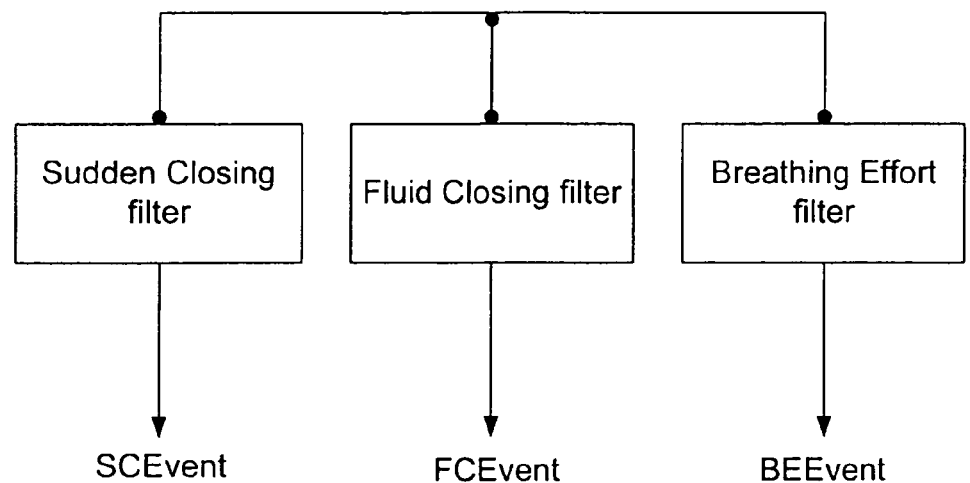
Figure 16:
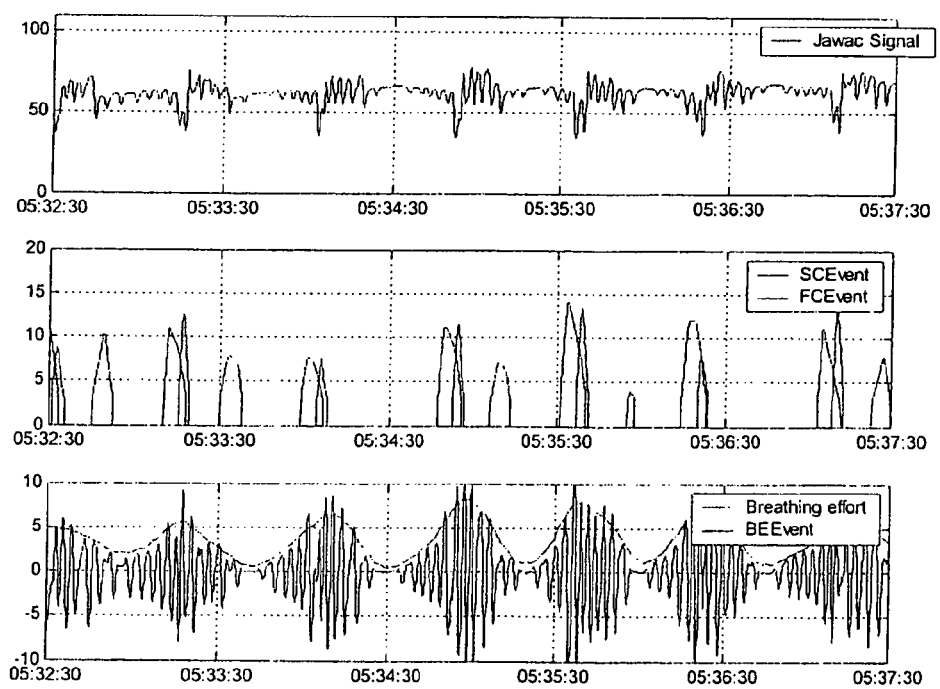
FIG. 16 reproduces mouth movement signals.

The objective of this first step (A) is to use filtering techniques that make it possible to reveal the essential characteristics of apneas. These steps are specified in FIG. 15. These characteristics are known and described in the thesis by Prof. R. Poirrier. The output of each filter is also a signal containing events. An event is a marker of a potential characteristic of an apnea and it is the combination of these events that will be used for classification of the different types of apnea. FIG. 16 illustrates this method. The distance measurement signal obtained from the sensors is depicted in the first part of the figure in a time window of five minutes. Here, the value one hundred means that the mandible is completely closed and zero means that the mandible is wide open.

The Sudden Closing Event (SCEvent) signal is a signal obtained by calculating the measurement signal mean difference. The SCEvent signal is only the positive part of the results of the mean difference revealing the places where the mandible is closed suddenly. The amplitude of this derived signal shows the magnitude of this closure. This signal is, consequently, a sudden closing event marker.

Figure 17:
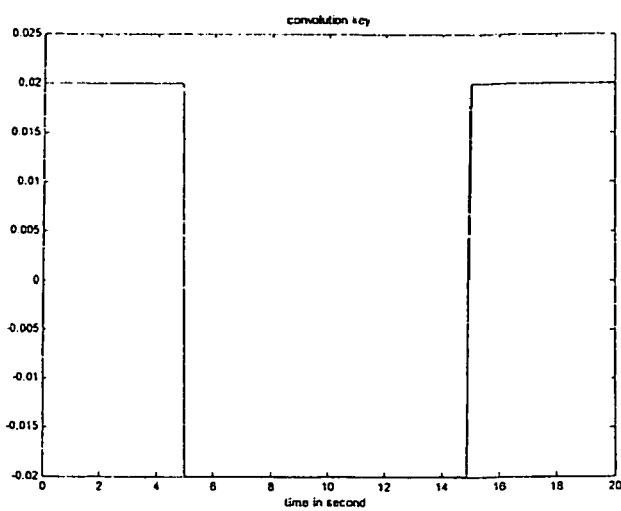
FIG. 17 illustrates a convolution key.
Figure 18:
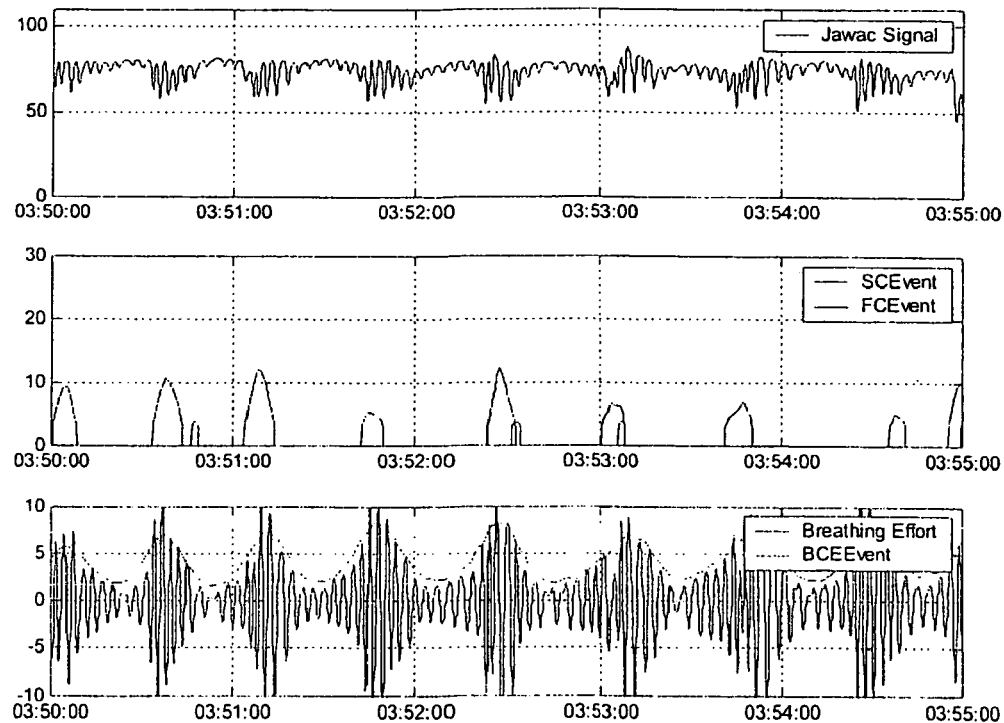
FIG. 18 illustrates the result of the convolution.

The Fluid Closing Event (FCEvent) signal is a signal obtained by convolution of the measurement signal and a convolution key. This convolution key is reproduced in FIG. 17. The objective of this convolution is to reveal the fluid variations of the measurement signal which represent an opening of the mandible followed by an opposite and similar closing. The result of the convolution is reproduced in FIG. 18 (FCEvent).

The last signal obtained by filtering is the BCEvent signal. First of all the measurement signal is filtered with a bandpass filter in the breathing frequency band (typically 0.2 to 0.4 Hz). The result of the filtering is what is referred to as the Breathing Effort signal. Consequently, the BCEvent signal is simply the upper envelope of the Breathing Effort signal. All these three derived signals are the markers of a possible end of an apnea event.

Figure 14B:
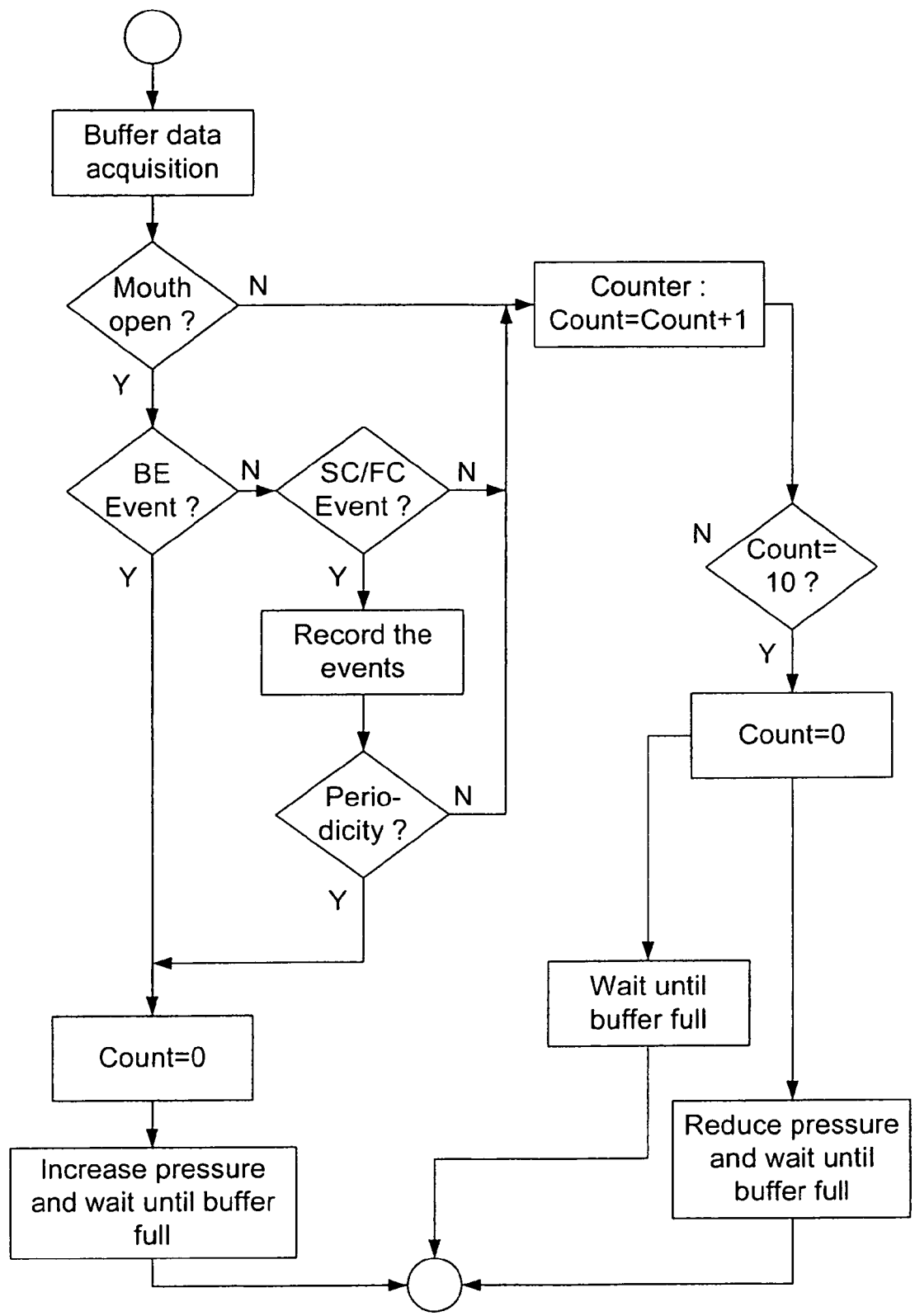
Figure 19:
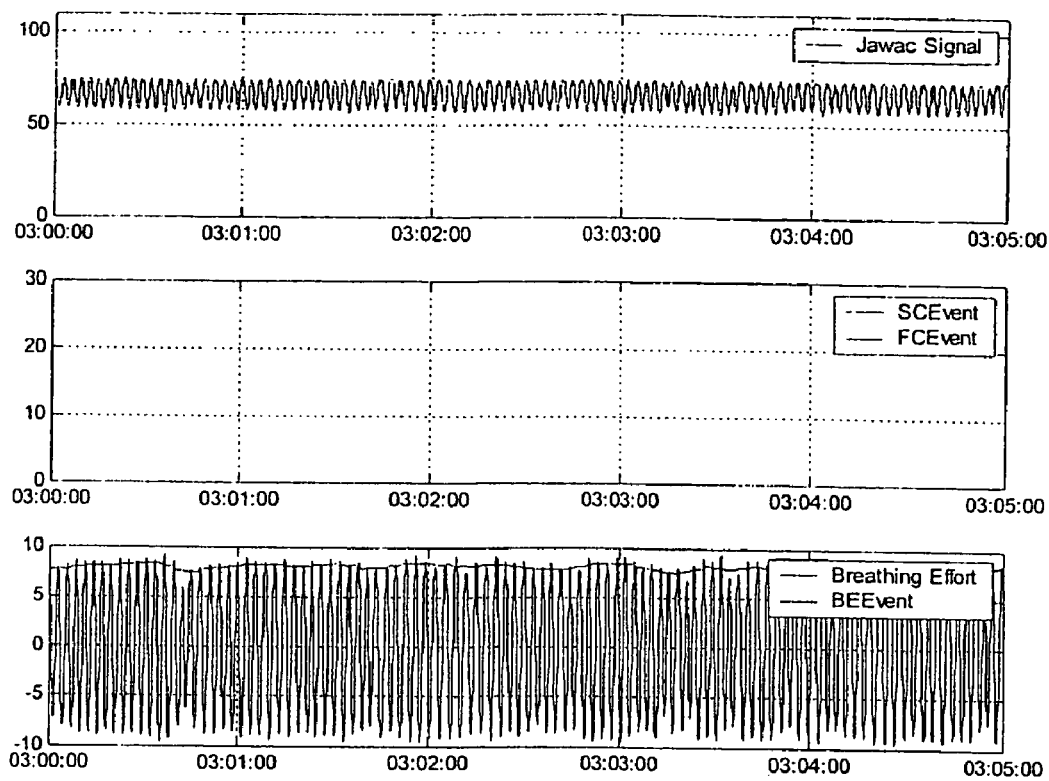
FIG. 19 depicts a period of snoring.

The second objective of this stage A (FIG. 14) is to detect the periods of snoring. Snoring is defined as a sinusoidal signal oscillating at the breathing frequency (typically 0.2 to 0.4 Hz) and of constant amplitude. FIG. 19 depicts a period of snoring.

The following step of the algorithm is used to delimit all the candidate apnea events. The duration of an apnea is generally defined in a time window of 10 to 90 seconds. The three derived signals (SCEvent, FCEvent, BEEvent) are first of all used to reject the events that do not represent apneas. An event is accepted if one of the following two conditions is fulfilled:

The presence of SCEvent and BEEvent in the time window under consideration;

The presence of FCEvent and BEEvent in the time window under consideration.

Next, for all the events accepted, the time window under consideration is searched through backwards in order to look for where the apnea is assumed to have started. Typically, the apnea starts when the BBEvent starts to increase in the time period under consideration. This is the case for hypopneas and obstructive apneas. In the case of central or mixed apneas, the apnea starts with no breathing effort and, in this case, the event BBEvent is the signature of the end of the apnea. Consequently it is necessary to derive another signal so as to delimit central and mixed apneas. In the time period under consideration, the places where the breathing effort is zero are noted. The NEBEvent event signal marks the absence of a breathing effort at the start of an apnea.

The last derived signal is used for detection of upper airway resistance syndromes (UARS): in the time window under consideration of an apnea, it is noted if the mean opening of the mandible is linear during the whole of the apnea.

The second important aspect of this step is to find the portions of signal where one of the above three events is repeated with a strict time period. The periodicity of an event will be used to confirm the presence of an apnea burst.

The aim of this step is to classify all the apneas delimited. The following binary table is used. For each apnea delimited, the apnea type is characterized by the presence or absence of all the events in the region delimited. The table reproduced in FIG. 20 illustrates this.

Two rules are used to confirm the above classification. The above classification may contain graphoelements which are not strictly speaking apneas. So as to obtain a specificity and satisfactory sensitivity of the algorithm, only graphoelements that satisfy at least one of the following two rules are accepted:

Rule 1: All apneas detected in a "periodic" region will be accepted.

Rule 2: Each classified graphoelement that contains a BEEvent event above a specified threshold will be accepted. Here, isolated apneas that are detected but do not have a sufficient breathing effort will be rejected.

In a similar manner to the detection of sleep respiratory disorders, sensors are used to regulate the pressure of a continuous positive air pressure apparatus.

The principle of the method proposed is as follows:

1) The data are collected in a buffer. The length thereof is defined so as to contain at least one apnea (typically 10 to 90 seconds).

2) It is first of all verified that the mouth is more or less closed (typically 80%).

3) If the mouth is open, it is verified that the following events are present: BEEvent, SCEvent and FCEvent. The periodicity is also verified for confirmation. If such an event is observed, the pressure is increased and all the following data are awaited.

4) If the mouth is more or less closed (usually 85% of closure), the possibility is given of using a different timescale for reducing the pressure. The reduction in pressure is slower than the increase. Here, it is considered that the reduction in pressure is ten times slower than the increase. The ratio between the increase and the reduction can be adapted for each person.

The same distance detector can be used in any other application requiring monitoring or analysis of the movement of a joint, by placing the two elements of the sensor either side thereof.

Figure 21:
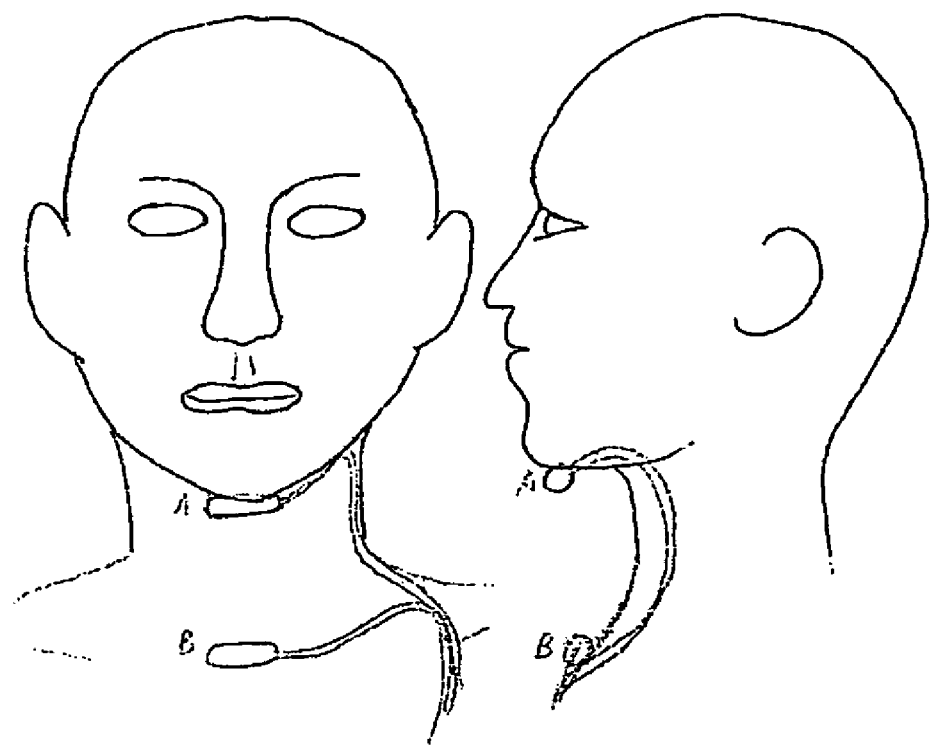
FIG. 21 illustrates the position of sensors for detecting Parkinson's disease.

Monitoring the development of Parkinson's disease in a patient is one example. Within this context, it is useful to record, over one or more days, the state of the patient in order to detect situations of tremor, rigidity and stooping. To this end, the distance sensor can be placed at the chin and thorax, as shown in FIG. 21, in order to measure head movement characteristics. Statistics can then be produced to judge the efficacy of a treatment, for example. Alternatively, the sensors can be placed at the elbow, hip, or knee with similar effects.

- The rigidity state is detected by an analysis of variability of the signal over given periods. The procedure can for example be calculation of the variance of the signal. A variance of small value is representative of a rigidity state.
- The stooping state is a rigidity state where the mean distance value measured is moreover very small.
- A tremor state can be detected by a spectral analysis of the signal. The appearance of a predominant spectral component in the distance signal over a given period is representative of a tremor state.

Periodic movement of the limbs is another sleep disorder. The use of the same distance detector for detecting these movements is possible. The principle is altogether similar to the case of monitoring Parkinson's disease. However, the analysis instead looks for isolated movements and their periodicity rather than general states.

There is plentiful literature on the means of detecting the loss of vigilance of a person, in particular while driving a vehicle. The distance sensor presented here is used for such measurements according to two methods:

a. Measuring the Nodding of the Head

The appearance of a state of drowsiness is accompanied by relaxation of the neck muscles which has the effect, in the vertical position, of a progressive lowering of the head. When the person realizes this, they react by suddenly lifting their head again. Placing the distance sensor on the chin and thorax, in accordance with FIG. 21, makes it possible to detect these events. The analyzer therefore proceeds by identifying sudden movements upwards, which constitutes a particular case of the analysis.

b. Measuring the Opening of the Eyelid

Component miniaturization makes it possible to place one of the elements of the distance sensor on the eyelid, the other being placed under or above the eye. During a progressive loss of vigilance, more frequent blinking of the eyelids is observed, as well as a progressive decrease in the mean opening of the eyelid. The detection of these events also constitutes a particular case of the analysis.

Safety applications require control of the activation of a machine or a device as a function of distance, so as to avoid false operation or avoid unintended usage. The use of this distance sensor with selective energizing allows this use. In this case, the switch of the energizing circuit can serve as the activation request of the user, but the actual activation will be carried out only by a hardware or software decision element after verification of the distance at which the activation device is situated. Activation of different devices according to distance is also possible, for example, but not solely, for displaying different warning messages.

The invention claimed is:

1. Distance measuring device comprising an emitter and a receiver, said emitter being arranged to produce a magnetic field by means of a resonant circuit having a resonant frequency, said receiver being arranged to pick up at said resonant frequency the magnetic field emitted by the emitter and convert the strength of the magnetic field picked up into a first signal having an energy value, said emitter being arranged to produce said magnetic field intermittently, each emission having a predetermined energy, said receiver being connected to a detector arranged to determine a distance measurement signal representing the distance between the emitter and the receiver, wherein said detector is arranged to determine said distance measurement signal by correlation of said first signal with a second predetermined signal having a waveform representing a signal to be picked up as obtained in the absence of perturbation by the receiver, said second signal comprising a time window having a predetermined duration and comprising at least an initial sub-period, an intermediate sub-period and a final sub-period, said second signal being an alternating signal synchronized with the first signal and whereof the amplitude is attenuated during the initial and final periods and substantially at a maximum during the intermediate period, said detector being arranged to implement said correlation by multiplication and integration with said second signal.

2. Distance measuring device as claimed in claim 1, wherein said detector is arranged to implement said correlation by multiplication and integration with said second signal, which second signal is formed by said waveform representing a sinusoidal waveform in synchronization with the first signal itself multiplied by a Tukey window with reduced taper factor.

3. Distance measuring device as claimed in claim 1, wherein said detector is arranged to implement said correlation by multiplication and integration with said second signal, which second signal is formed by said waveform representing a square waveform in synchronization with the first signal.

4. Distance measuring device as claimed in claim 1, wherein said emitter is housed in a case and arranged to produce said magnetic field outside said case with a power less than 1 mTesla.

5. Di stance measuring device as claimed in claim 1, wherein said emitter comprises an induction coil and a capacitor connected in series with one another and connected by means of electrical conductors to an energizing circuit, said energizing circuit comprising a voltage source and a resistor connected, through said electrical conductors, in series with the induction coil and the capacitor, said energizing circuit also comprising a switching element making it possible to connect said electrical conductors to one another.

6. Distance measuring device as claimed in claim 5, wherein said energizing circuit, the induction coil, and the capacitor form an autonomous unit with respect to the receiver.

7. Sleep disorder detector comprising a distance measuring device as claimed in claim 1, wherein said device is mounted on a support arranged to be applied onto the head of a living being so as to measure movements of the mouth.

8. Sleep disorder detector as claimed in claim 7, wherein said detector comprises an analyzer having an input connected to the device and arranged to receive said distance measurement, said analyzer being arranged to divide said distance measurement signal into fractional parts and apply time windows to each fractional part of the distance measurement signal thus obtained, said detector also comprising a memory for storing a series of signal forms characterizing in a time window movements of the mouth of a living being, said analyzer being arranged to compare said fractional parts of the distance measurement signal with each of said forms of the series and to produce a detection signal in the event of correspondence between said fractional part and said form, the detection signal also comprising an indicator indicating the form having led to said correspondence.

9. Sleep disorder detector as claimed in claim 8, wherein said series comprises a first form indicating a sudden closing of the mouth, a second form indicating a slow opening of the mouth followed by a slow closing of the mouth, and a third form indicating an increase in the amplitude of the signal at the breathing frequency followed by a decrease in the signal at the breathing frequency.

10. Sleep disorder detector as claimed in claim 8, wherein said analyzer is arranged to produce an apnea signal when for the same window the detection signal indicates both a first and a third form or indicates both a second and a third form.

11. Sleep disorder detector as claimed in claim 8, wherein said series comprises a fourth form indicating snoring.

12. Sleep disorder detector as claimed in claim 8, wherein said detector comprises an analyzer having an input connected to the device and arranged to receive said distance measurement signal, said analyzer being arranged to identify, in said distance measurement signal, signal forms representing brief and recurrent events and to produce a detection signal at each occurrence of such signals, the detection signal also comprising an indicator indicating the form having led to said detection signal.

13. Sleep disorder detector as claimed in claim 12, this detector comprising a decision element using said detection signal to provide an indication of insufficient, correct or excessive treatment for the targeted sleep disorders.

14. Movement analyzer comprising a distance measuring device as claimed in claim 1, wherein said device is mounted on a support arranged to be applied around a joint of a living being so as to measure the characteristics and/or statistics of the movements of this joint.

15. Detector of periodic movements of limbs during sleep comprising a movement analyzer as claimed in claim 14, wherein said analyzer arranged to identify, in said distance measurement signal, signal forms representing brief and recurrent events and to produce a detection signal at each occurrence of such signals, the detection signal also comprising an indicator indicating the form having led to said detection signal.

16. Equipment for monitoring the development of Parkinson's disease comprising a movement analyzer as claimed in claim 14, wherein said analyzer is arranged to identify, in said distance measurement signal, signal forms representing tremor, rigidity and stooping states in order to produce a detection signal, the detection signals also comprising an indicator indicating the form having led to said detection signal.

17. Equipment for detecting a loss of vigilance comprising a movement analyzer as claimed in claim 14, wherein said measuring device is placed so as to measure the inclination of the head and said analyzer is arranged to identify, in said distance measurement signal, events of slow inclination and sudden lifting of the head, in order to produce a detection signal.

18. Equipment for detecting a loss of vigilance comprising a movement analyzer as claimed in claim 14, wherein said measuring device is arranged so as to measure the amplitude of opening of the eyelids and said analyzer is arranged to identify, in said distance measurement signal, events of recurrent blinking of the eyelids and a state of progressive decrease in the mean amplitude of opening of the eyelids, in order to produce a detection signal.

19. Distance measuring device as claimed in claim 1, wherein said emitter is housed in a case and arranged to produce said magnetic field outside said case with a power less than 1 µTesla.

* * * * *